US010157472B2

(12) United States Patent
Young et al.

(10) Patent No.: US 10,157,472 B2
(45) Date of Patent: Dec. 18, 2018

(54) APPARATUS AND PROCESSES FOR CORN MOISTURE ANALYSIS AND PREDICTION OF OPTIMUM HARVEST DATE

(71) Applicant: RAYTHEON COMPANY, Waltham, MA (US)

(72) Inventors: Darrell L. Young, Falls Church, VA (US); Charlotte DeKeyrel, Leesburg, VA (US); Michael Henry Lewis, Leesburg, VA (US)

(73) Assignee: RAYTHEON COMPANY, Waltham, MA (US)

( * ) Notice: Subject to any disclaimer, the term of this patent is extended or adjusted under 35 U.S.C. 154(b) by 0 days.

(21) Appl. No.: 15/067,750

(22) Filed: Mar. 11, 2016

(65) Prior Publication Data
US 2016/0300363 A1 Oct. 13, 2016

Related U.S. Application Data

(60) Provisional application No. 62/132,274, filed on Mar. 12, 2015.

(51) Int. Cl.
*G06K 9/00* (2006.01)
*G06T 7/40* (2017.01)
(Continued)

(52) U.S. Cl.
CPC ............ *G06T 7/408* (2013.01); *G01N 21/00* (2013.01); *G01N 21/55* (2013.01); *G01N 33/025* (2013.01);
(Continued)

(58) Field of Classification Search
None
See application file for complete search history.

(56) References Cited

U.S. PATENT DOCUMENTS 4,954,783 A 9/1990 Spry
2009/0046890 A1* 2/2009 Hausmann ............ G06T 7/0012
382/100
(Continued)

FOREIGN PATENT DOCUMENTS

CN 102033043 A 4/2011
EP 1332354 B1 8/2003
WO 2009023110 A1 2/2009

OTHER PUBLICATIONS

Kandala: "nondestructive Moisture Sensing in Peanuts by NIR Reflectance", IEEE 2009, pp. 1-5.*
(Continued)

*Primary Examiner* — Weiwen Yang
(74) *Attorney, Agent, or Firm* — Lando & Anastasi, LLP

(57) ABSTRACT

Methods and apparatus are provided for determining moisture content of corn. In one example, a method includes processing a captured image of an ear of corn using a threshold value to create a segmented binary image comprising a first plurality of blobs, determining at least one characteristic of a plurality of corn kernels represented by the first plurality of blobs, and estimating a moisture value for the ear of corn based on the at least one characteristic of the plurality of corn kernels. In some embodiments, the method includes generating a luminance intensity profile across a region of the captured image containing at least one corn kernel in the plurality of corn kernels, computing a derivative of the luminance intensity profile; an determining, with reference to the derivative of the luminance intensity profile, a location of a boundary of the at least one corn kernel.

20 Claims, 10 Drawing Sheets

(51) Int. Cl.
  *G01N 21/00* (2006.01)
  *G01N 33/02* (2006.01)
  *G06T 7/00* (2017.01)
  *G01N 21/55* (2014.01)
  *G06N 5/04* (2006.01)
  *G06T 7/60* (2017.01)
  *G06T 7/11* (2017.01)
  *G06T 7/90* (2017.01)
  *G06T 7/136* (2017.01)

(52) U.S. Cl.
  CPC ............ *G06N 5/04* (2013.01); *G06T 7/0002* (2013.01); *G06T 7/11* (2017.01); *G06T 7/136* (2017.01); *G06T 7/60* (2013.01); *G06T 7/90* (2017.01); *G01N 2201/06113* (2013.01); *G06T 2207/30128* (2013.01)

(56) References Cited

U.S. PATENT DOCUMENTS

2012/0263394 A1* 10/2012 Fujiwara ............... H04N 1/387
                                                          382/266
2015/0015697 A1* 1/2015 Redden ............... G01N 33/0098
                                                          348/89
2016/0078570 A1* 3/2016 Ethington .......... G06Q 10/1097
                                                          705/7.21
2016/0225135 A1 8/2016 Young et al.

OTHER PUBLICATIONS

Liu: "Variation in Corn Stover Yield and Fule Quality With Harvest Time", IEEE 2009, pp. 1-6.*
Huaipu Song et al. "Nuclear Magnetic Resonance Imaging of Transient Three-Dimensional Moisture Distribution in an Ear of Corn During Drying", Cereal Chemistry, vol. 67. No. 6; Jan. 1, 1990 (Jan. 1, 1990), pp. 580-584.
International Search Report and Written Opinion from PCT Application No. PCT/US2016/022055 dated Aug. 22, 2016.
Mahale Bhagyashree et al. "Rice quality analysis using image processing techniques", International Conference for Convergence for Technology—2014. IEEE. Apr. 2014 (Apr. 6, 2014), pp. 1-5.
Schmidt et al. "Applications of magnetic resonance in food science", Critical Reviews in Food Science and Nutrition. Taylor & Francis. USA, vol. 36. No. 4, Jan. 1, 1996 (Jan. 1, 1996), pp. 357-385.

* cited by examiner

APPARATUS AND PROCESSES FOR CORN MOISTURE ANALYSIS AND PREDICTION OF OPTIMUM HARVEST DATE

RELATED APPLICATIONS

This application claims priority under 35 U.S.C. § 119(e) to U.S. Provisional App. No. 62/132,274, entitled "APPARATUS AND PROCESSES FOR CORN MOISTURE ANALYSIS AND PREDICTION OF OPTIMUM HARVEST DATE," filed Mar. 12, 2015, which application is incorporated herein by reference in its entirety.

BACKGROUND

Farmers have long wrestled with the question of when a field of corn is ready to be harvested. Corn loses moisture after it reaches the point of maturity. Corn that is harvested too early has a high moisture content, and cannot be stored without spoiling. The operators of grain elevators where many farmers bring their harvested corn may therefore refuse to store corn whose weight attributable to water, or moisture content, is 16% or higher, for fear it will spoil everything in the store. Instead, the farmer is charged a fee for the operator to "dry down" the corn to an acceptable level by heating the corn to remove excess moisture. The profit margin on corn can be so slim that the drying-down fees to bring the moisture content of "under-dried" corn down even slightly may erase the farmer's profits, or cause the farmer to suffer a loss.

Yet there are also disadvantages to "over-drying" by letting corn stand in the field too long before harvesting. Each day the corn goes unharvested increases losses due to lodged or dropped ears, and increases the risk that pests, hail, tornadoes, or other adversity will damage or destroy the crop. Moisture loss also decreases sale weight. Over-dried kernels are also more brittle and prone to break, resulting in a lower quality rating. Finally, harvesting may also be less efficient on over-dried corn, as combines work best on corn having a moisture content of 20-22%.

While the drying-down fees associated with under-drying are quantifiable and predictable, the above-mentioned costs associated with over-drying are not as apparent. Psychological aversion mechanisms may therefore explain why many farmers err on the side of over-drying by leaving their crops for longer than necessary, and suffer the associated costs.

Current methods of determining the moisture content of corn involve the use of electronic moisture meters, or comparing the weight of the corn before and after it is heated in an oven. In addition to being cumbersome, such techniques do not predict an optimum time to harvest the corn, nor do they take into account the unseen attrition costs of over-drying the corn.

SUMMARY OF THE INVENTION

According to one aspect of the present invention, a method for determining moisture content of corn includes a processing a captured image of an ear of corn using a threshold value to create a segmented binary image comprising a first plurality of blobs, determining at least one characteristic of a plurality of corn kernels represented by the first plurality of blobs, and estimating a moisture value for the ear of corn based on the at least one characteristic of the plurality of corn kernels. According to one embodiment, determining at least one characteristic of the plurality of corn kernels represented by the first plurality of blobs includes generating a luminance intensity profile across a region of the captured image containing at least one corn kernel in the plurality of corn kernels, computing a derivative of the luminance intensity profile; and determining, with reference to the derivative of the luminance intensity profile, a location of a boundary of the at least one corn kernel.

According to another embodiment, determining the at least one characteristic of the plurality of corn kernels represented by the first plurality of blobs includes determining an average kernel width of a plurality of horizontally adjacent corn kernels in the plurality of corn kernels in the captured image, determining an average horizontal gap between a plurality of horizontally adjacent corn kernels in the plurality of corn kernels in the captured image, and determining a relationship of the average width to the average horizontal gap.

According to one embodiment, includes processing a second captured image of a second ear of corn using a threshold value to create a second segmented binary image comprising a second plurality of blobs, determining a second at least one characteristic of a second plurality of corn kernels represented by the second plurality of blobs, estimating a second moisture value for the second ear of corn based at least in part on the at least one characteristic of the second plurality of corn kernels, and determining an exponential decay curve that fits the first moisture value and the second moisture value using a least squares fitting technique. According to another embodiment, includes determining, for each of a plurality of candidate target moisture values, an estimated number of days by which a moisture value of corn will equal the candidate target moisture value, determining for each of the plurality of candidate target moisture values, an estimated cost to harvest the corn on the estimated target date, and identifying an optimal target moisture value among the plurality of candidate target moisture values for which the cost to harvest the corn on the estimated target date for the candidate target moisture value is minimized.

According to one embodiment, determining for each of the plurality of candidate target moisture values, the estimated number of days by which the moisture value of corn will equal the candidate target moisture value includes estimating an estimated number of growing degree units (GDUs) that must be accumulated to cause the corn to have the optimal target moisture value, and estimating the estimated number of days over which the number of GDUs will be accumulated. According to another embodiment, estimating the number of days over which the number of GDUs will be accumulated comprises accessing historical meteorological information relating to a geography in which the ear of corn is located. According to another embodiment, includes determining an actual number of GDUs accumulated during a day, and revising the estimated number of days over which the number of GDUs will be accumulated.

According to one embodiment, estimating the moisture value for the ear of corn based on the at least one characteristic of the plurality of corn kernels comprises estimating an average depth of a plurality of indentations on the plurality of corn kernels in the captured image. According to another embodiment, estimating the moisture value for the ear of corn based on the at least one characteristic of the plurality of corn kernels includes determining a first reflectance value of light having a first wavelength from a stalk of the ear of corn, the first wavelength being sensitive to moisture, determining a second reflectance value of light having a second wavelength from the stalk of the ear of corn, the second wavelength being non-sensitive to moisture, and comparing the first reflectance value and the second reflectance value. According to another embodiment, determining the first reflectance value of light and the second reflectance value of light each comprises directing a laser beam at the stalk of the ear of corn.

According to another aspect of the present invention, an image processing system includes a memory, an image receiving component, and a processor configured to process a captured image of an ear of corn using a threshold value to create a segmented binary image comprising a first plurality of blobs, determine at least one characteristic of a plurality of corn kernels represented by the first plurality of blobs, and estimate a moisture value for the ear of corn based on the at least one characteristic of the plurality of corn kernels. According to one embodiment, the image processing system of claim 12, wherein the processor is further configured to determine the at least one characteristic of a plurality of corn kernels represented by the first plurality of blobs by acts includes generating a luminance intensity profile across a region of the captured image containing at least one corn kernel in the plurality of corn kernels, computing a derivative of the luminance intensity profile, and determining, with reference to the derivative of the luminance intensity profile, a location of a boundary of the at least one corn kernel.

According to another embodiment, the processor is further configured to determine at least one characteristic of the plurality of corn kernels represented by the first plurality of blobs by acts includes determining an average kernel width of a plurality of horizontally adjacent corn kernels in the plurality of corn kernels in the captured image, determining an average horizontal gap between a plurality of horizontally adjacent corn kernels in the plurality of corn kernels in the captured image, and determining a relationship of the average width to the average horizontal gap. According to another embodiment, the image receiving component is a camera of a mobile device, wherein the processor is further configured to determine a first reflectance value of light having a first wavelength from a stalk of the ear of corn, the first wavelength being sensitive to moisture, determine a second reflectance value of light having a second wavelength from the stalk of the ear of corn, the second wavelength being non-sensitive to moisture; and compare the first reflectance value and the second reflectance value. According to another embodiment, includes a laser directing device, wherein determining the first reflectance value of light and the second reflectance value of light each comprises directing a laser beam at the stalk of the ear of corn.

According to one embodiment, the processor is further configured to process a second captured image of a second ear of corn using a threshold value to create a second segmented binary image comprising a second plurality of blobs determine at a second least one characteristic of a second plurality of corn kernels represented by the second plurality of blobs; and estimate a second moisture value for the second ear of corn based at least in part on the at least one characteristic of the second plurality of corn kernels. According to another embodiment, the processor determines, for each of a plurality of candidate target moisture values, an estimated number of days by which a moisture value of corn will equal the candidate target moisture value, determines for each of the plurality of candidate target moisture values, an estimated cost to harvest the corn on the estimated target date, and identifies an optimal target moisture value among the plurality of candidate target moisture values for which the cost to harvest the corn on the estimated target date for the candidate target moisture value is minimized. According to another embodiment, the processor estimates an estimated number of growing degree units (GDUs) that must be accumulated to cause the corn to have the optimal target moisture value, and estimates the estimated number of days over which the number of GDUs will be accumulated. According to another embodiment, determines an actual number of GDUs accumulated during a day, and revises the estimated number of days over which the number of GDUs will be accumulated.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Figure 1:
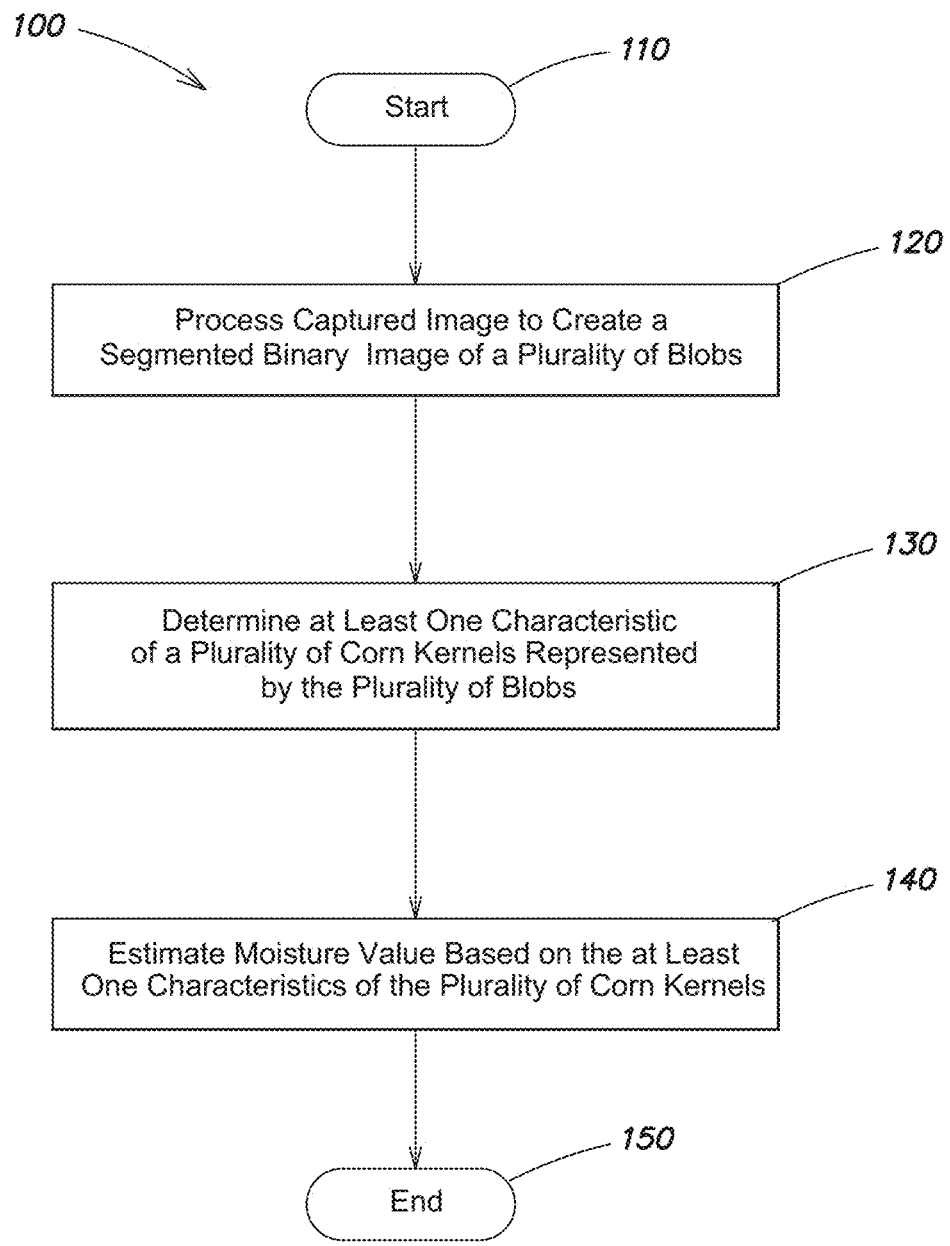
FIG. 1 is a flow diagram of one example of determining moisture content of an ear of corn.

The ability to process images of ears of corn to accurately estimate the moisture content of corn enables farmers to more easily and accurately estimate an optimal harvest date and schedule resources accordingly. Selecting an optimal harvest date that minimizes the cost to the farmer can lead to savings of at least $0.04/bushel, or $8.00/acre. A 10,000 acre farm could therefore cut seasonal costs by at least $80,000 by selecting an optimal harvest date according to the systems and methods disclosed herein.

Topographical maps and soil data may be analyzed to identify representative locations from which to select ears of corn for moisture analysis. Aspects and embodiments are directed to capturing an image of a selected ear of corn and processing it to create a binary image according to a threshold value. The image may be processed by computing an extended-minima transform or H-minima transform. The binary image is used to identify the location of kernels on the ear of corn. Using those locations, the captured image can be analyzed to measure the gaps between kernels. The size of these gaps increases as kernels lose moisture and shrink; the measurement can therefore be used to estimate a moisture content of the corn. "Dents" on the surface of the kernel, which are also indicative of moisture loss, may also be measured, and the moisture content of the stalks and husks of the corn may also be detected by measuring their reflectance at different wavelengths.

Aspects and embodiments are directed to using two or more moisture measurements to generate a moisture model predicting the corn's moisture content over time. While there are known exponential decay models for moisture loss in corn as a function of the number of days since the corn reached maturity, certain present embodiments include moisture models as functions of the cumulative average temperatures accumulated during the corn's growth. The two or more moisture measurements may be optimally scheduled to yield the most useful measurements in generating the model and refining it over time. One or more adaptive moisture measurements may be optimally scheduled based on earlier moisture measurements.

Aspects and embodiments are directed to generating a cost model in connection with the moisture model that estimates the cost to the farmer to harvest the corn at various moisture contents. The cost model takes into account the costs associated with under-drying (such as drying-down fees) as well as over-drying (increased loss due to fallen or lodged ears, pests, damage, etc.), and is a function of the accumulated heat required to reach the optimal moisture value. An optimal moisture value is identified that minimizes the cost to the farmer, thereby maximizing profit. Known temperature/weather profiles for the geographic region can be used to predict how many days it will take for the corn to dry down to the optimal moisture value, allowing the farmer to determine an estimated harvest date. As the corn continues to mature, actual weather/temperature readings replace the estimates in the temperature/weather profile, and the optimal moisture value and the estimated harvest date can be adjusted accordingly.

Further aspects and embodiments are directed to sharing such estimated and actual moisture values and model parameters with other farmers (e.g., as subscribers of a system), allowing group members to benefit from individual measurements by refining their own estimates accordingly.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

According to some embodiments, an image of an ear of corn is processed by thresholding the image to create a binary image (i.e., one in which each pixel is one of two colors, typically black and white). The binary image is made up of a number of "blobs," or contiguous regions of similar colors or other values, with each blob corresponding to a kernel of corn. The moisture content of the ear of corn can be estimated with reference to the characteristics of the kernels of corn (as identified by the blobs), such as the locations of their centers and their perimeters, the gaps between the kernels, and the appearance of the kernels. For example, the gaps between kernels may indicate how much the kernels have shrunk due to moisture loss; the size of those gaps may be used to determine the moisture content. As another example, kernels of corn may have a concave "dent" on their top surface as they lose moisture, so the moisture content may be determined from the depth, size, or other characteristic of the dent.

Selecting the ear(s) of corn on which to perform the claimed methods may be done in a manner intended to select ears representative of different soil conditions and topographies where the crop is located. Topographical maps with elevation data may be retrieved (e.g., from a database) and analyzed by a system practicing the claimed methods. In some embodiments, watershed algorithms are applied to identify the fewest number of sample points that spans the most representative parts of the field from a topographical perspective. A user may be presented with a plan, such as a map showing the locations where sample ears should be gathered. The user may be allowed to change the number of points and generate a new plan with that number of points, or modify the proposed plan by manually deleting or adding points. Soil maps may also be consulted as part of the topographical analysis, so that soil makeup, acidity, moisture content, and other aspects of the land may be taken into account for different portions of the cornfield.

FIG. 1 is a flow diagram for one example of a method 100 for determining moisture content of an ear of corn.

Method 100 begins at step 110.

At step 120, a captured image of an ear of corn is processed using a threshold value to create a segmented binary image comprising a plurality of blobs.

An image of an ear of corn is obtained by a computer system, and preliminary processing is performed to generate a modified image to be used as input to subsequent steps. In some embodiments, the image of the ear of corn may be captured by a digital camera, or by a mobile device (e.g., a cell phone or tablet) with a camera and image-capturing capabilities. The smartphone or tablet may be configured to detect an ear of corn in the image in real-time or near-real-time, and to provide instructions to the user of the device regarding the positioning of the device. For example, the device may indicate to the user that the ear of corn should be held horizontally, or that the user should move the device closer to or further from the ear of corn in order to achieve optimal composition of the image.

In some embodiments, the image may be adjusted to compensate for the flash setting of the camera, or the lighting/shadow conditions in the captured image. For example, the image itself or metadata about the image may be examined to determine if the flash was used, and the exposure may be adjusted accordingly. In other embodiments, the mobile device may provide an indication that an image suitable for processing cannot be captured due to current lighting conditions, or may provide an indication that a captured image is not suitable for processing due to the lighting conditions in the captured image. The mobile device may display to the user an indicator (such as an on-screen icon) that the lighting conditions should be changed (e.g, by moving into a more suitably-lit location). In some embodiments, the camera flash may be automatically enabled or disabled according to the ambient lighting conditions.

In other embodiments, the image is not directly captured, but may be received over a network, on a disk, or otherwise provided to the system for processing.

In some embodiments, the size of the image may also be validated or modified as necessary. For example, if the image is of too low a resolution, size, contrast, or sharpness, it may be assumed that the method cannot be performed on the image in a manner yielding sufficiently accurate results. If the image does not meet certain requirements, the process may be terminated by the system, and an error message may be displayed to the user indicating that the image is deficient, as well as information identifying the deficiency. In some embodiments, the image may be downsampled to a lower resolution (e.g, 2 megapixels) that reduces file size while still providing sufficient resolution for the image processing steps described herein. Downsampling the image to a standardized resolution may also simplify subsequent processing steps, as there would be no need to provide for the processing of images having different resolutions.

The image may also be preliminarily processed to verify the existence and location of a probable ear of corn in the image. In some embodiments, the image is analyzed to locate a region matching the expected characteristics of a photograph of corn, such as a generally yellow to white color and an overall shape associated with ears of corn. In other embodiments, the spatial variation in pixel intensities (i.e., the pixel texture) in a region is detected and analyzed. Texture analysis may allow an ear of corn to be detected in the image even where the characteristic of the corn or ambient conditions such as lighting make recognition of the ear by color or other characteristic unreliable or impossible. The image may then be "smeared" by adjusting each pixel according to an averaged value of the surrounding pixels; doing so may reduce or eliminate any inconsistencies due to lighting or other conditions.

To further streamline processing, the image can be cropped to the region where an ear of corn is detected, resulting in an image substantially filled by the ear of corn. The image may also be straightened through rotation or other orientation change so that a centerline along the longitudinal axis of the ear is parallel to the upper and lower edges of the image. The image may also be resized to standardized dimensions to reduce the complexity of later processing steps. In one embodiment, the image is resized to 1400 pixels wide by 400 pixels high; however, numerous other image sizes can be used. In some embodiments, adaptive histogram equalization (AHE) or contrast-limited adaptive histogram equalization (CLAHE) is performed on the image. The image analysis and processing steps described herein may be performed by the MATLAB package offered by The Mathworks, Inc., of Natick, Mass.

Processing an image of an ear of corn is discussed in U.S. application Ser. No. 15/011,004, filed on Jan. 29, 2016 and titled "APPARATUS AND PROCESSES FOR CLASSIFYING AND COUNTING CORN KERNELS," which application is hereby incorporated by reference in its entirety.

Figure 2A:
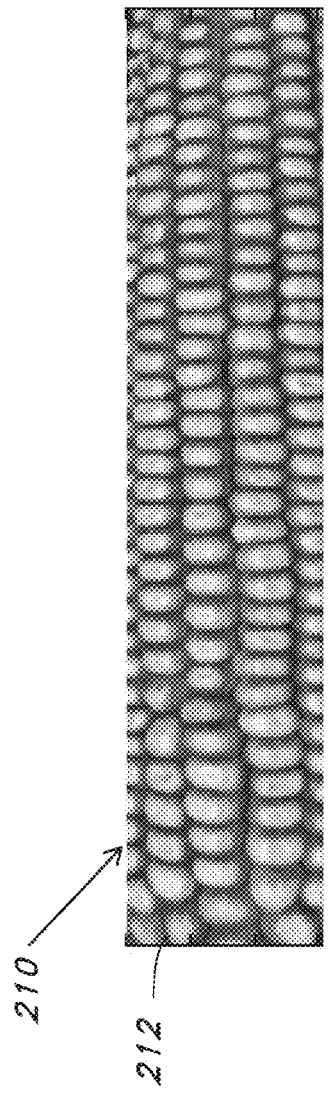
FIG. 2A illustrates an exemplary cropped captured image of an ear of corn according to aspects of the invention.

FIG. 2A shows an exemplary cropped image 210 of an ear 212 of corn.

Referring again to FIG. 1, once any preliminary processing has been completed, the image is thresholded to create a binary image (i.e., one in which each pixel is one of two colors, typically black and white). In particular, each pixel of the image is assigned a white value if the pixel's luminance value is higher than a given threshold luminance value, or a black value if the pixel's luminance value is lower than the given threshold luminance value. In some embodiments, the binary image is generated by computing an extended-minima transform or H-minima transform.

By selecting an appropriate threshold, a binary image made up of a number of blobs is created in which the individual blobs reflect the shape and size of the corresponding individual kernels in the photograph. In one embodiment, each kernel of corn may appear as a contiguous white region (i.e., a blob) on a black background. The location of the blob in the binary image indicates the location of a corresponding kernel of corn in the captured image. For example, the coordinates of a blob in the binary image may be stored as the coordinates of the corresponding kernel of corn in the captured image. In some embodiments, coordinates may be stored identifying the approximate center of the kernel of corn, which may be determined by locating the "center of mass" of the corresponding blob.

Figure 2B:
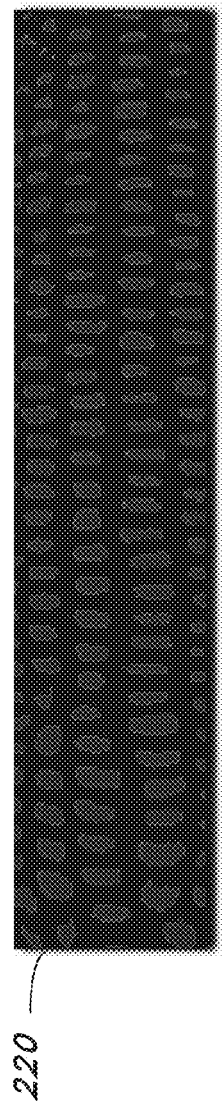
FIG. 2B illustrates an exemplary binary image generated from the cropped captured image of FIG. 2A using optimal threshold values according to aspects of the invention.

FIG. 2B shows the binary image 220 generated from the exemplary cropped image 210 of the ear 212 of corn shown in FIG. 2A.

Referring again to FIG. 1, at step 130, at least one characteristic of a plurality of corn kernels represented by the plurality of blobs is determined, and at step 140, a moisture value for the ear of corn is estimated based on the at least one characteristic of the plurality of corn kernels.

Using the location of the plurality of corn kernels in the captured image as determined in the previous step, other characteristics of the plurality of corn kernels may be determined. For example, considering an image in which the long axis of an ear of corn is aligned horizontally (as in FIGS. 2A and 2B), the horizontal thickness T and the vertical width W may be determined. W and T of a kernel have been found to be linearly related to the moisture of a kernel having a moisture percentage $M_c$ between 9% and 30%, such that:

$$T \text{ (mm)} = 0.0301 M_c + 3.6732, \text{ and}$$

$$W \text{ (mm)} = 0.0364 M_c + 7.975.$$

In some embodiments, one or more rows of horizontally adjacent kernels may be identified by fitting the coordinates of the kernels in the captured image to one or more generally horizontal curves using least-square analysis.

Figure 3:
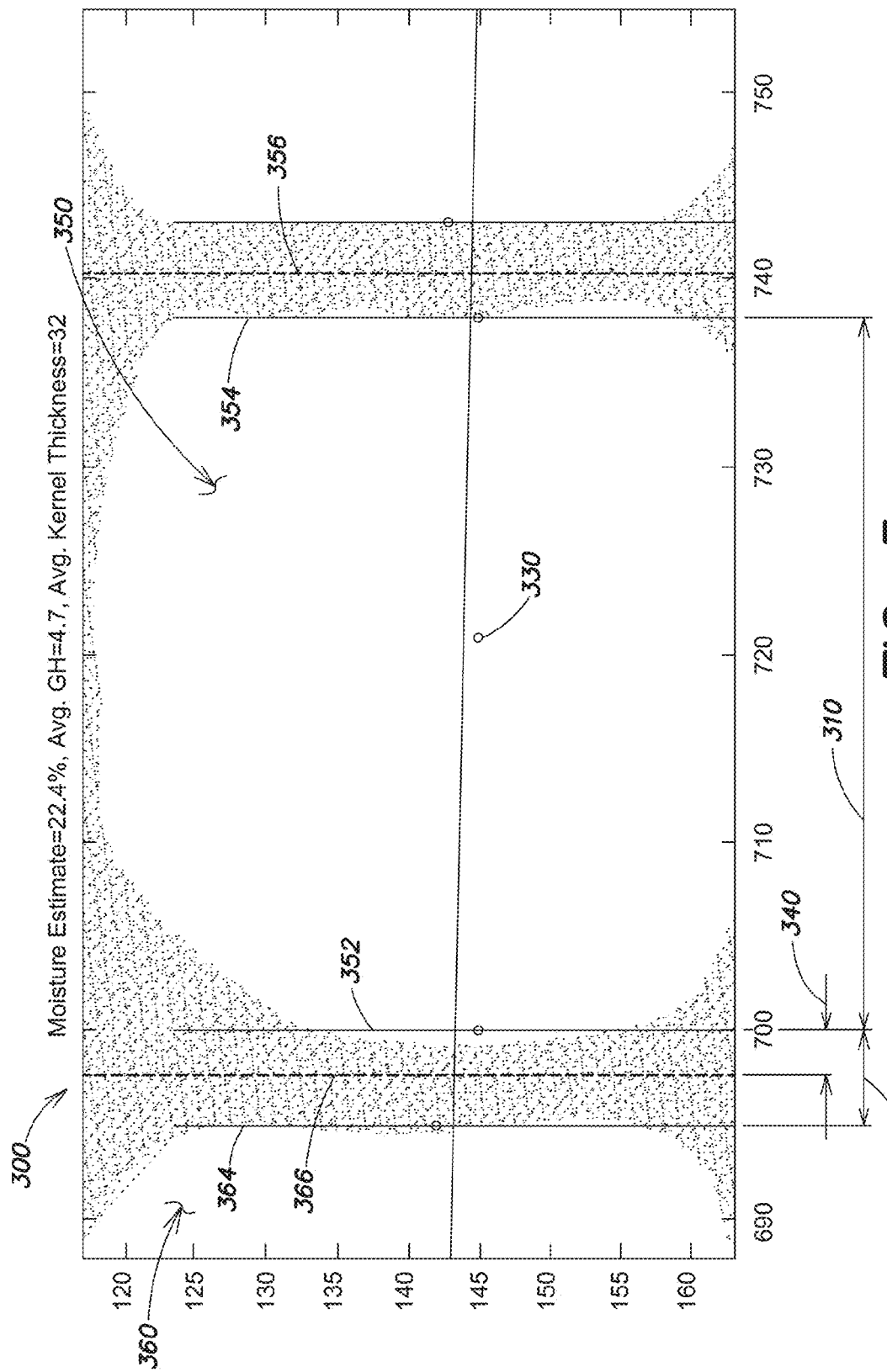
FIG. 3 illustrates a detailed view of a cropped captured image showing an ear of corn.

As corn kernels dry out, they undergo post-maturity linear shrinkage. In some embodiments, therefore, the relative horizontal gaps between one or more kernels in a row may be used to estimate the moisture content of the kernels. Relative horizontal gap $G_H$ may be expressed as horizontal gap width (the amount of space between a kernel and an adjacent kernel) divided by the thickness T of the kernel. FIG. 3 shows a close-up of a kernel 350 on ear 210 in FIG.

2A. The center 330 of the kernel 350 was located in the previous step. The kernel 350 has a thickness 310 of T, and has is separated from an adjacent kernel 360 by a horizontal gap width 320. The relative horizontal gap $G_H$ can therefore be expressed as the horizontal gap width 320 divided by the thickness 310.

To determine the thickness 310 of the kernel 350 and the horizontal gap width 320 between kernels 350 and 360, the boundaries of the kernels are determined. The variation between the bright kernels and the dark gaps between them can be used to identify the boundaries of the kernels. In some embodiments, a horizontal intensity profile is generated. The horizontal intensity profile represents a line graph showing the luminance intensity moving horizontally across a region of the captured image. A horizontal intensity profile may be generated for each of a plurality of kernels, for example, by starting from the center 330 of the kernel 350 and extending horizontally in each direction in an amount sufficient to encompass the boundaries on each side of the kernel 350.

A derivative of each horizontal intensity profile may be determined, representing the slope of the luminance (i.e., the amount by which the luminance is changing) at each point. The most negative derivative value on each side of the center 330 of the kernel 350 can be expected to correspond to the point on the top or side of the kernel where the relatively bright top portion of the kernel 350 meets the relatively shadowed side portion of the kernel 350. This point on either side of the center 330 represents the boundaries 352, 354 of the kernels. In some embodiments, a minimum 366 of the horizontal intensity profile between the boundaries 352, 364 of adjacent kernels may also be determined. At the minimum 366, the slope of the horizontal intensity profile is at its flattest, representing the low luminance (i.e., shadowed) area in the gap between the kernels. A second minimum 356 adjacent the boundary 354 on the other side of the kernel, and additional adjacent other kernels, may also be determined.

In some embodiments, the thickness T can be calculated as the distance between boundary 352 and boundary 354, and the horizontal gap width G 320 can be calculated as the distance between boundary 352 of kernel 350 and boundary 364 of kernel 360. These measurements can be determined for each of a plurality of kernels in the captured image.

In some embodiments, outlier values of T and G are removed from further consideration. Outlier values may be those that exceed certain defined thresholds, or that vary from a statistical threshold, such as being greater than one standard deviation different from the average values of T and G. Once the outlier values are removed, an average $T_{avg}$ of all T values and an average $G_{avg}$ of all G values are determined. Relative horizontal gap $G_H$ is calculated as $G_{avg}/T_{avg}$.

The estimated moisture content $M_H$ (given as a percentage) of the corn can then be calculated as a function of $G_H$, namely, $M_H = 32 - 64 G_H$.

In other embodiments, the distance from the boundary of the kernel to the minimum of the horizontal intensity profile may be used to estimate the moisture content of the corn. For example, the gap width G' 340 may be determined as the distance in pixels from the minimum 366 to the boundary 352. The thickness T, as calculated above, is the distance in pixels between boundary 352 and boundary 354. These measurements can be determined for each of a plurality of kernels in the captured image.

In some embodiments, outlier values of T and G' are removed from further consideration. Outlier values may be those that exceed certain defined thresholds, or that vary from a statistical threshold, such as being greater than one standard deviation different from the average values of T and G'. Once the outlier values are removed, an average $T_{avg}$ of all T values and an average $G'_{avg}$ of all G' values are determined. Relative horizontal gap $G'_H$ is calculated as $G'_{avg}/T_{avg}$.

The estimated moisture content $M_H$ (given as a percentage) of the corn can then be calculated as a function of $G'_H$, namely, $M_H = (109 \times G'_H) - 1.33$.

In other embodiments, the concavity or "dent" in the top surface of the kernel may be determined, and used to estimate moisture content. Such concave "dents" form as the kernel loses moisture, so the moisture content may be estimated from the depth, size, or other characteristic of the dent. Characteristics of the dent may be determined in much the same manner as the boundaries of the kernel are detected as discussed above. In particular, variations in luminance can be detected between the relatively brighter pixels on the "rim" of the dent and the relatively darker pixels in the interior of the dent.

Figure 4A:
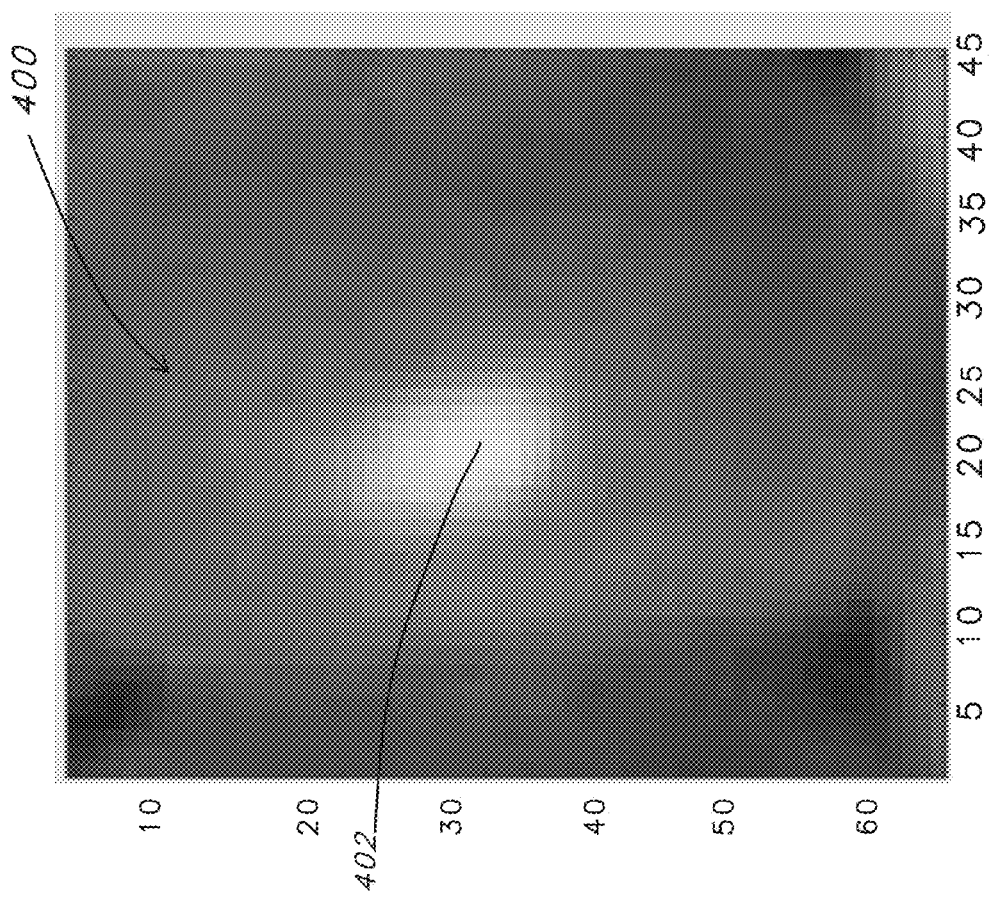
FIG. 4A shows an image of a corn kernel.
Figure 4B:
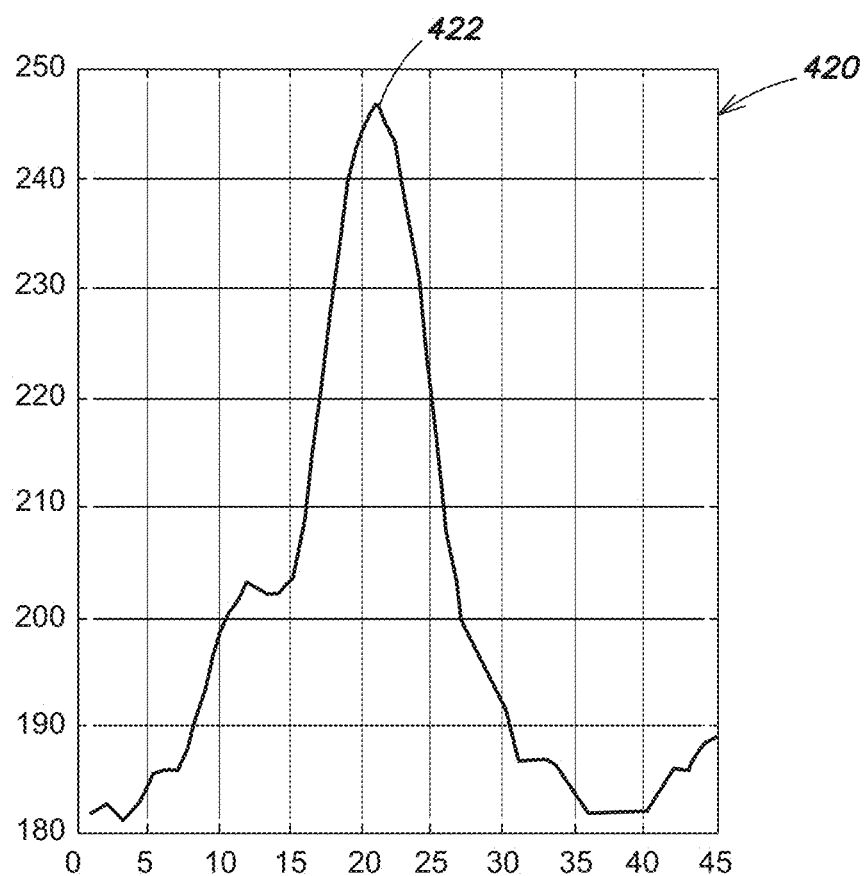
FIG. 4B shows a luminance intensity profile for the corn kernel of FIG. 4A.
Figure 4C:
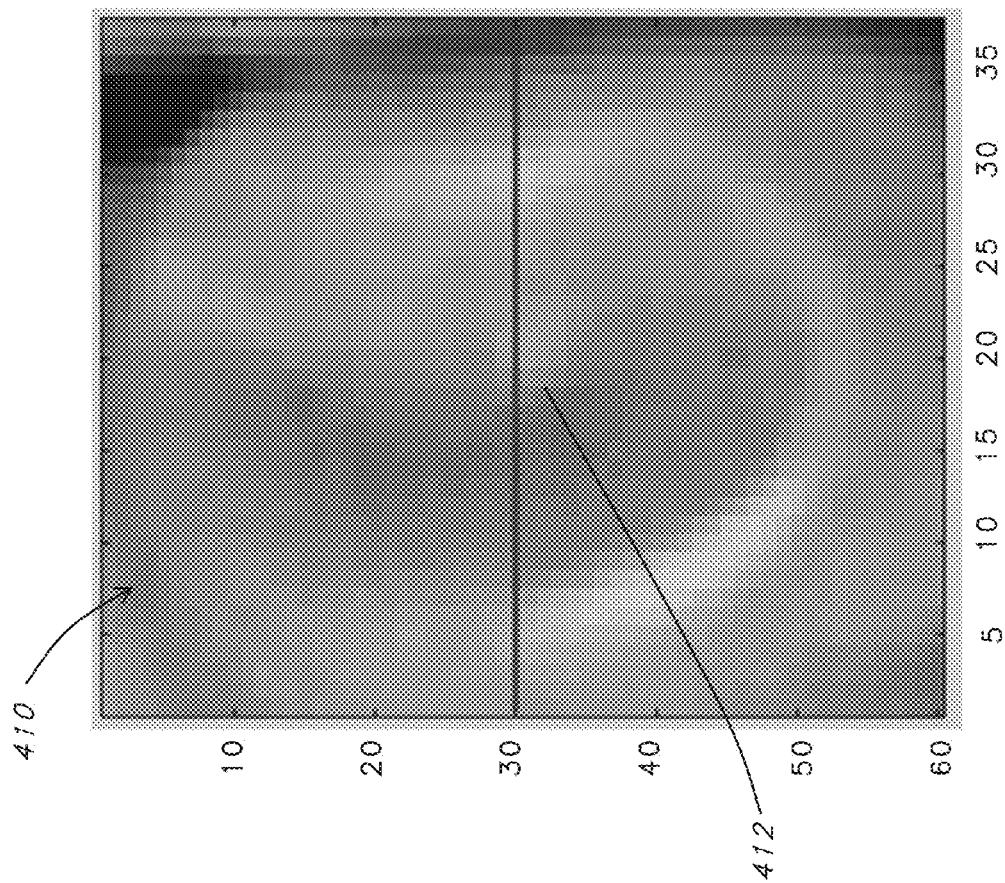
FIG. 4C shows an image of another corn kernel.
Figure 4D:
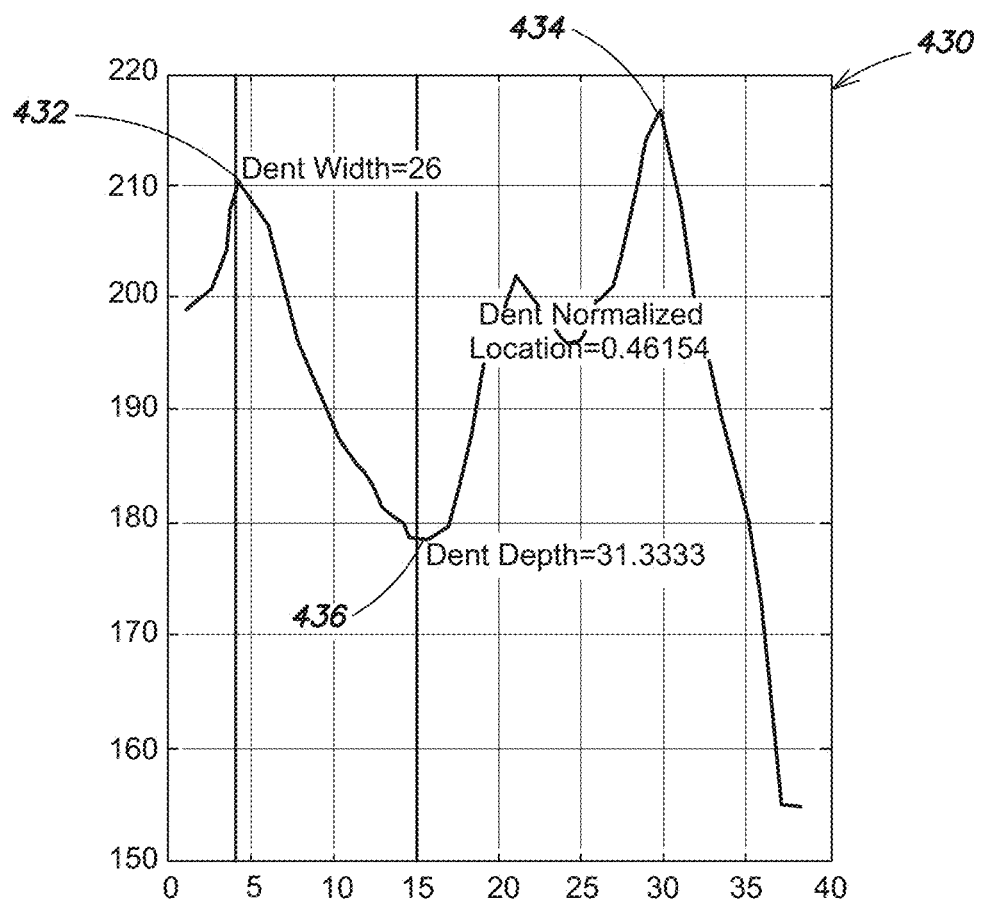
FIG. 4D shows a luminance intensity profile for the corn kernel of FIG. 4C.

FIGS. 4A and 4C illustrate a relatively high-moisture kernel 400 and a relatively low-moisture kernel 410, respectively. The high-moisture kernel 400 has a convex smooth top 402, whereas the low-moisture kernel 410 has a "dent," i.e., a concave smooth top 412. A horizontal intensity profile of the pixels in an image of a kernel can be generated. The horizontal intensity profile represents a line graph showing the luminance intensity moving horizontally across the kernel. Horizontal luminance profiles 420, 430 for kernels 400, 410 can be seen in FIGS. 4B and 4D, respectively.

Horizontal luminance profiles can be used to identify characteristics of the kernel, such as the shape or depth of the dent. As the depth of the dent is inversely proportional to the moisture content of the kernel, the moisture content can be estimated from the depth of the dent. For example, in horizontal luminance profile 420 for high-moisture kernel 400, it can be seen that the intensity increases towards the center of the kernel to a local maxima 422, corresponding to the natural reflectivity of the smooth, flat surface. By contrast, in horizontal luminance profile 430 for low-moisture kernel 410, a number of luminance intensity maxima and minima can be determined. For example, the rim of the dent in kernel 410 can be seen at maxima 432, 434, and the approximate deepest point of the dent can be seen at minima 436. By determining an intensity gradient from minima 436 to maxima 432, 434, the depth of the dent can be estimated. The depth of the dent can be used, in turn, to estimate the moisture content.

The moisture content of corn kernels is directly related to the moisture content of the leafy stalk and husk of the ear of corn on which the kernels are located. Therefore, in some embodiments, the moisture content of the leafy stalks and/or husks of corn may be estimated, and may be used to estimate the moisture content of the corn kernels. Measuring the moisture content of the stalks eliminates the need to remove the husk from the corn, thereby allowing the method to be carried out on an entire cornfield (or portion thereof) from a distance.

In one embodiment, the moisture content of the stalk may be determined by measuring an amount of light reflecting off the stalk at a wavelength sensitive to moisture, and comparing that measurement to an amount of light reflecting off the stalk at a wavelength not sensitive to moisture. For example, the reflectance of the stalk at 1900 nm (a wavelength sensitive to moisture) may be compared to the reflectance of the stalk at 1800 nm (a wavelength not sensitive to moisture). In other embodiments, wavelengths of 980 nm and 800 nm may be used, respectively. The ratio of the two reflectances may be used to determine the moisture content of the stalk, which may be used in turn to determine the moisture content of the kernels on the attached ear of corn.

In some embodiments, a specialized camera, or specialized camera accessory for a mobile device (such as a smartphone or tablet) may be used to determine the reflectance of the stalk at certain wavelengths. In other embodiments, a standard camera of a mobile device may be used with or without modification, such as by removing the silicon filter from the lens. As mobile device cameras may not be sensitive enough in some lighting conditions to detect differences in reflectance at the different wavelengths, a laser device may be provided, and laser beams of each wavelength directed at the husk for a very short duration (e.g., 1/30 second). The reflectance of the laser beam may be more easily measured by the mobile device.

Returning to FIG. 1, method 100 ends at step 150.

Method 100 yields an initial moisture value of the kernel $M_0$. Predicted moisture measurements can be determined for a future time as an exponential decay function of the initial moisture value; the cumulative heat experienced by the kernel after "silking," when corn silk first emerges from the husk; and an exponential decay coefficient. In one example, an estimate of a future moisture M can be calculated by the "moisture equation" as:

$$M = M_0 e^{-KX}$$

where $M_0$ is the initial moisture value of the kernel, K is an exponential decay coefficient, and X is a number of growing degree units (GDUs) after first silking. In an example using the Fahrenheit scale, the number of GDUs for a given day can be calculated as a function of the average temperature (i.e., the average of the high temperature $T_{max}$ and the low temperature $T_{min}$) for that day, as follows:

$$GDU = \frac{T_{max} + T_{min}}{2} - T_{base}$$

where $T_{base}$ is a constant of 50° F., and where $T_{max}$ cannot exceed 86° F. and $T_{min}$ cannot go below 50° F. The number of GDUs for each day in a period of time can be added to determine the cumulative GDUs experienced during that period. The values for $T_{base}$, $T_{max}$, and $T_{min}$ may vary by location, and are given here for illustrative purposes only.

In some embodiments, the exponential decay coefficient K may be determined based on historical conditions and the strain of corn to which it is being applied. For example, the value of K to be used for a given year for a particular strain of corn may be published or otherwise obtainable from third-parties or otherwise.

In other embodiments, however, the value of K may be estimated by taking a number of moisture and GDU values over time. As discussed above, method 100 estimates a single moisture value for kernels on an ear of corn in an image at the time the image was captured. By repeating the steps of method 100 at one or more intervals after the initial run, a number of moisture values for corn in a particular location can be determined over time. The cumulative number of GDUs for the season at the time of each moisture measurement may also be determined, either by directly measuring the high and low temperatures during each sampling day and all intervening days, or by accessing temperature or GDU information directly from a database. In some embodiments, the value of K may be adjusted based on lighting conditions in the captured images from which one or more moisture measurements were estimated. For example, where shadows in a captured image may tend to result in over-estimations of moisture measurements, the value of K may be adjusted to compensate.

In one example, when n moisture measurements $y = [M_1 M_2 \ldots M_n]$ and concurrent cumulative GDU measurements $x = [GDU_1 \ GDU_2 \ \ldots \ GDU_n]$ have been taken, it may be possible to solve the moisture equation for $M_0$ (by refining $M_0$ to adjust for inaccurate timing of the first reading). The moisture equation can be expressed in the form of a polynomial mx+b as $\log(y) = \log(M_0) - KX$. Where n=2, $M_0$ and K can be determined algebraically. Where n>2, the moisture equation is overdetermined, and $M_0$ and K can be estimated using a least-squares or regression model.

A number of moisture and GDU measurements may be taken over a period of time. More frequent measurements may yield more accurate results to a point, but may incur time and cost associated with the sampling. An optimized schedule for taking moisture measurements may help balance the accuracy vs. time/cost considerations in a beneficial way.

According to a preferred embodiment, three moisture measurements are taken at different times after the corn has reached maturity. In some embodiments, the moisture measurements are estimated according to the steps of method 100. The first and second moisture measurements are taken at fixed times with respect to the corn's lifecycle, such as 55 and 65 days after first silking. The third measurement is adaptive, and is scheduled based on the first and second moisture measurements. In other embodiments, the moisture measurements are taken by existing methods, such as a corn moisture meter. The first and second moisture measurements are taken at fixed times with respect to the corn's lifecycle, such as 10 and 40 days after first silking. The third measurement is adaptive, and is scheduled based on the first and second moisture measurements.

Having taken actual or estimated moisture measurements, an estimated date on which the corn will have optimal moisture content can be determined by applying the values of $M_0$ and K (estimated as discussed above using a least-squares or regression model) to the moisture equation, solving for the number of GDUs required to reach that optimal moisture content, and converting that number of GDUs to an estimated harvest date.

When the estimated harvest date is determined, the third moisture measurement may be scheduled for a certain period of time in advance of that estimated harvest date (e.g., 7 days before the estimated harvest date). The results of the third moisture measurement (and concurrent GDU measurement) may be used to further refine the values of $M_0$ and K, which may consequently change the estimated harvest date if the third moisture measurement varies from its expected value due to intervening weather conditions or other factors. In some embodiments, additional measurements may be scheduled where confidence in the current values of M0 and K, or the fit of additional measurements to the current cost equation, are insufficient.

In other embodiments, moisture measurements may be taken on two, three, or more fixed dates, and no adaptive measurements are taken.

The ideal moisture content at which corn should be harvested is approximately 15.5%. If the corn is harvested too early, and has a higher moisture content when presented at a grain elevator for storage, the corn must be heated to dry it out sufficiently to avoid spoilage. The cost to the farmer of such drying treatment can quickly erode any expected profit the farmer could have earned. On the other hand, waiting too long to harvest unnecessarily increases the loss due to dropped ears and lodged stocks, as well as the risk of damage by pests, adverse or destructive weather such as tornadoes, and the like. In some situations, harvesting at a moisture content that varies from the ideal moisture content may be advantageous if doing so reduces the farmer's costs associated with under-drying or over-drying.

To determine the optimal moisture content at which to harvest the corn so as to minimize the cost according to a number of factors, a cost model may be employed. The cost model may estimate the cost to harvest the corn based on a number of inputs, including the moisture content at the time of harvest; the cost to dry corn having excessive moisture; the fractional daily loss due to dropped ears, lodged stalks, pest damage, and the like; the expected number of days until an optimal moisture content is reached; and the expected price-per-bushel earned for the harvested corn. The cost model may be run for a number of candidate optimal moisture content values within a certain acceptable range, and the candidate optimal moisture content value selected that minimizes the expected cost to the farmer.

Figure 5:
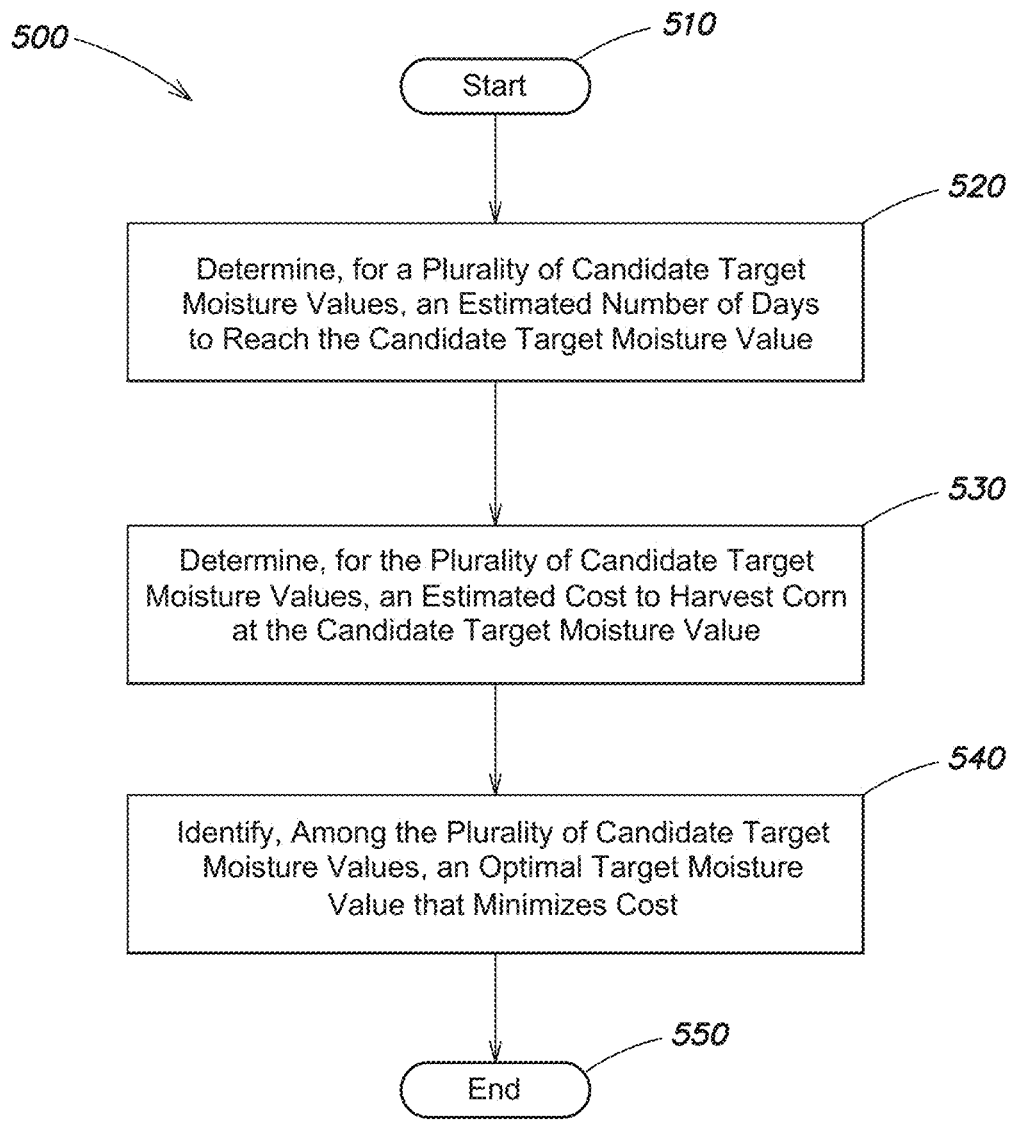
FIG. 5 is a flow diagram of one example of a process of determining an optimal moisture content of an ear of corn at which the farmer can harvest the corn at a minimum estimated cost.

FIG. 5 is a flow diagram for one example of a method 500 for determining an optimal moisture content of an ear of corn at which the farmer can harvest the corn at a minimum estimated cost.

Method 500 begins at step 510.

At step 520, an estimated number of days is determined, for a plurality of candidate target moisture values, after which the corn will reach the candidate target moisture value. In some embodiments, the candidate target moisture values may be selected from a range encompassing or near to an expected or known ideal moisture value. For example, if the ideal moisture value at which to harvest corn is 15.5%, the candidate target moisture values may range from 14.9% to 15.6% in increments of 0.1%.

For each candidate target moisture value, the estimated target date by which the corn will reach the candidate target value may be determined with reference to historical and/or predictive data. With $M_0$ and K having been estimated in previous steps, the moisture equation can be solved for X to determine the number of GDUs required to reach the candidate target moisture value M.

In some embodiments, a GDU profile for the geographic region is stored and accessed. The GDU profile records and/or predicts the number of GDUs accumulated each day for a range of dates in a particular geographic region. The GDU profile may be iterated through D days' worth of GDU profile data until the number of GDUs accumulated reaches or exceeds X. The candidate target value D is the number of days it is estimated to take for the corn to reach the candidate target moisture value. For example, where X (i.e., the estimated number of GDUs required to reach the candidate target moisture value) is 200, and the GDU profile estimates the total number of GDUs for the 77 days following first silking to be 200, then D is assigned a value of 77.

At step 530, an estimated cost to harvest the corn is determined for the estimated target date for each of the plurality of candidate target moisture values. A cost model may be used to calculate the cost of harvesting the corn at the time it has reached each of the candidate target moisture values $M_T$.

In some embodiments, the cost model may be expressed as:

$$C_T = c_1 + \max(M_T - 15.5, 0) + 2cDP + \max(15.5 - M_T, 0)P$$

Where $C_T$ is the estimated cost to harvest at the candidate target moisture value $M_T$, $c_1$ is the under-drying cost (i.e., the cost to dry per moisture percentage point), $c_2$ is over-drying cost (i.e., the fractional daily loss due to dropped ears, lodged stalks pest damage, etc.), D is the estimated number of days to reach $M_T$ as counted from the earliest possible harvest date, and P is the expected price-per-bushel the corn will fetch at sale.

The values of $c_1$, $c_2$, and P may vary due to market conditions, weather conditions, or other factors, and may be set or adjusted as necessary. In some embodiments, the values of $c_1$, $c_2$, and P may be provided via user input or a configuration file, or may be accessed via a database. In some embodiments, the under-drying cost of $c_1$ has a default value of $0.55/bushel, and the over-drying cost $c_2$ has a default value of $0.004/bushel.

Figure 6:
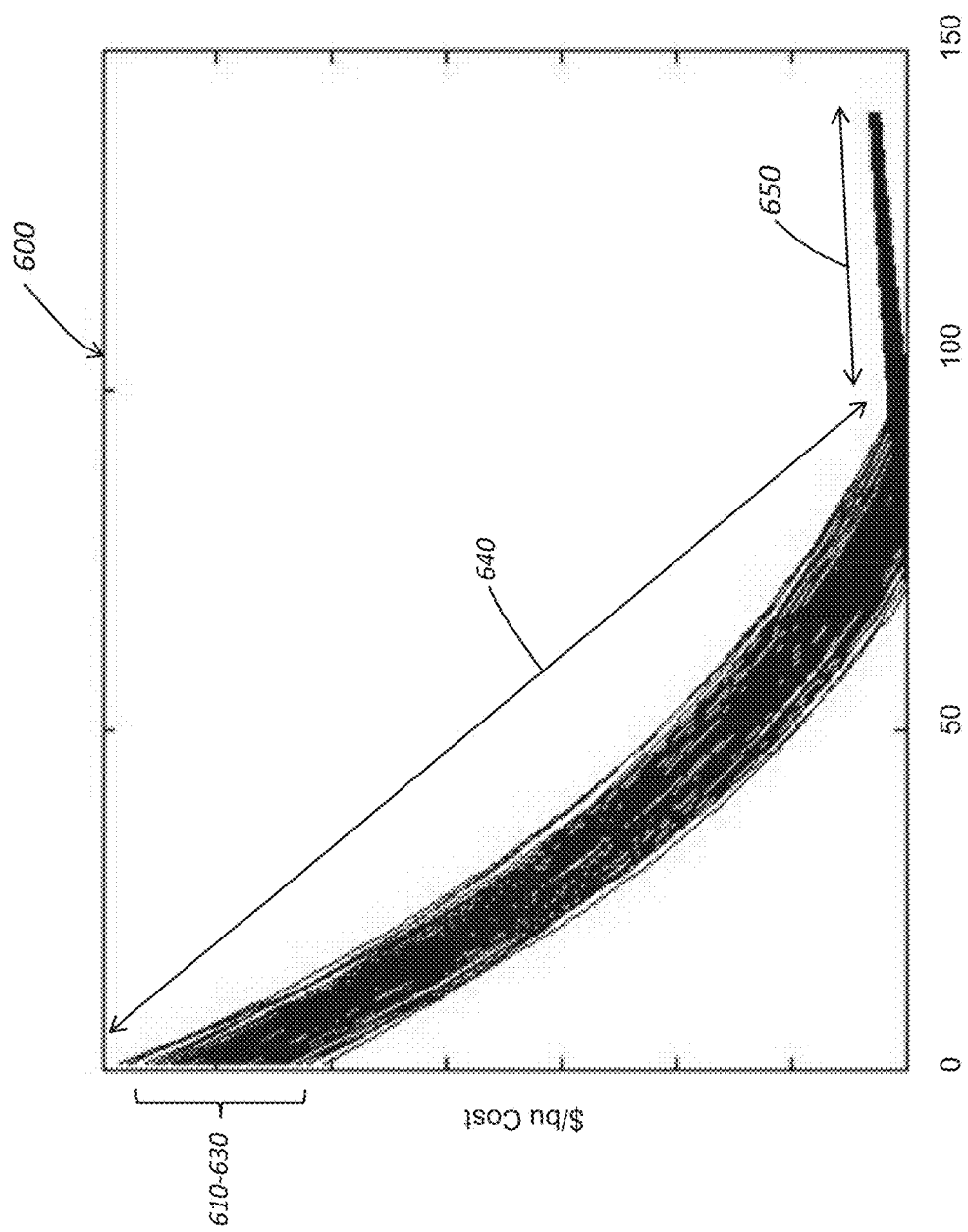
FIG. 6 is a graph of one example of a cost model for different candidate target moisture values over time.

FIG. 6 illustrates an example graph 600 showing a plurality of series 610-630 representing $C_T$ for different candidate target moisture values $M_T$ over time. As can be seen, each $C_T$ decreases for a time period 640 until a minimum cost is reached, and then begins increasing again for a time period 650.

Returning to FIG. 5, at step 540 an optimal target moisture value among the plurality of candidate target moisture values is identified for which the cost to harvest the corn on the estimated target date for the candidate target moisture value is minimized. The candidate target moisture value $M_T$ associated with the minimum value of $C_T$ determined in step 530 is identified as the optimal target moisture value. The optimal target moisture value and the estimated date on which the corn will reach the optimal target moisture value may be presented to a user via a user interface.

In some embodiments, the estimated GDU values in the GDU profile may be compared to the actual GDUs as measured each day, and the cost model and/or the estimated target date may be revised as a result. For example, where the number of GDUs during a period of time accumulate more quickly than predicted due to higher-than-average temperatures, the cost model may be re-run, and a different optimal target moisture value identified; the estimated target date may be moved earlier as a result. Actual solar radiation information, precipitation measurements and types, and other meteorological conditions may also be used to adjust the estimated target date.

In some embodiments, more than one candidate target moisture value $M_T$ may yield the minimum value for $C_T$; in other words, there may be a tie among candidate target moisture values $M_T$ such that there is an equally minimum cost to harvest at any of them. In that case, each of the values $M_T$ may be displayed to a user or otherwise output, or certain criteria may be applied to select among those candidate target moisture values. For example, a lower moisture content may be favored in order to minimize the weight (and thus the cost) of the corn as it is transported to market or storage. In another example, a higher moisture content may be favored, in that harvesting relatively early may be attractive. In yet another example, a harvest date associated with a candidate target moisture content may be selected due to the availability of storage space or rental equipment, such as combines, on that harvest date. In another example, a harvest date associated with a candidate target moisture content may be selected to allow the farmer to harvest fields having lower-moisture-content corn first, allowing higher-moisture-content corn to continue drying down. In yet another example, a harvest date associated with a candidate target moisture content may be selected based on a predicted market value of the corn on that date or a future date.

Method 500 ends at step 550.

In some embodiments, moisture measurements and/or GDU information is shared with other users. In some embodiments, a subscription model may be utilized, and the raw data may be automatically made freely available to all or select users, or may be anonymized and/or aggregated if desired for privacy or other reasons. For example, actual factors as measured when a farmer brings in a harvest of corn may be compared with the predictions made by the models described herein. For example, the actual moisture value as determined on the date of harvest may be compared with the predicted moisture value on the harvest date according to the prediction models described herein. The prediction models of other users may be updated as a result. For example, the values for $M_0$ and K may be further refined when a first farmer brings a crop in for harvest, and the K values of other farmers who have not yet been harvested may be refined as a result. In some embodiments, the first farmer may be compensated, through a subscription plan or by the later-harvesting farmers, in exchange for performing that early harvest that yielded information helpful to the later-harvesting farmers and/or the future runs of the model generally.

Figure 7:
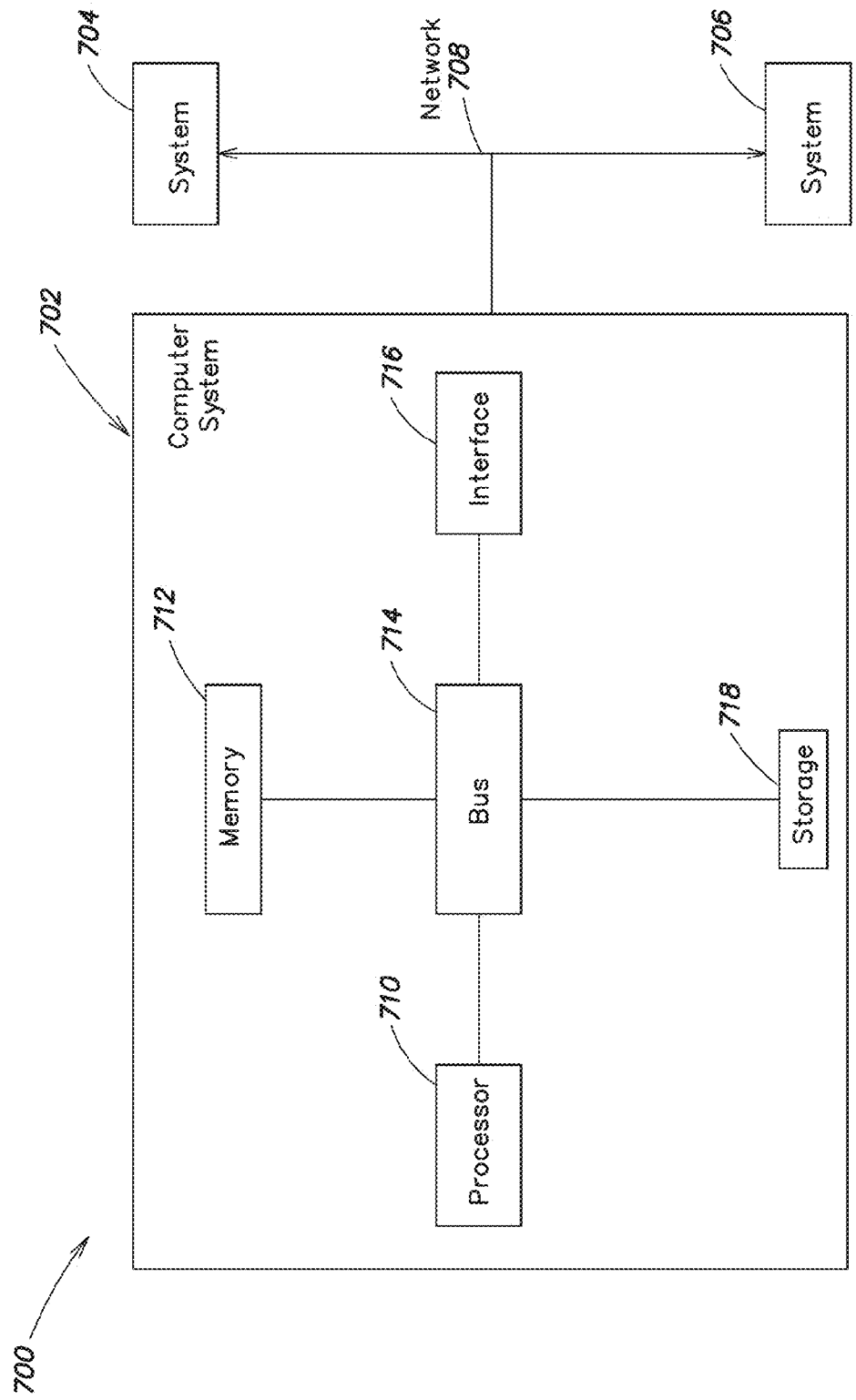
FIG. 7 is a block diagram of one example of a computer system on which aspects and embodiments of the present invention may be implemented.

FIG. 7 is a block diagram of a distributed computer system 700, in which various aspects and functions discussed above may be practiced. The distributed computer system 700 may include one or more computer systems. For example, as illustrated, the distributed computer system 700 includes three computer systems 702, 704 and 706. As shown, the computer systems 702, 704 and 706 are interconnected by, and may exchange data through, a communication network 708. The network 708 may include any communication network through which computer systems may exchange data. To exchange data via the network 708, the computer systems 702, 704, and 706 and the network 708 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS7, JSON, XML, REST, SOAP, CORBA HOP, RMI, DCOM and Web Services.

According to some embodiments, the functions and operations discussed for processing an image to determine the moisture content of corn can be executed on computer systems 702, 704 and 706 individually and/or in combination. For example, the computer systems 702, 704, and 706 support, for example, participation in a collaborative network. In one alternative, a single computer system (e.g., 702) can generate the three-dimensional synthetic viewpoint. The computer systems 702, 704 and 706 may include personal computing devices such as cellular telephones, smart phones, tablets, "fablets," etc., and may also include desktop computers, laptop computers, etc.

Various aspects and functions in accord with embodiments discussed herein may be implemented as specialized hardware or software executing in one or more computer systems including the computer system 702 shown in FIG. 7. In one embodiment, computer system 702 is a personal computing device specially configured to execute the processes and/or operations discussed above. As depicted, the computer system 702 includes at least one processor 710 (e.g., a single core or a multi-core processor), a memory 712, a bus 714, input/output interfaces (e.g., 716) and storage 718. The processor 710, which may include one or more microprocessors or other types of controllers, can perform a series of instructions that manipulate data. As shown, the processor 710 is connected to other system components, including a memory 712, by an interconnection element (e.g., the bus 714).

The memory 712 and/or storage 718 may be used for storing programs and data during operation of the computer system 702. For example, the memory 712 may be a relatively high performance, volatile, random access memory such as a dynamic random access memory (DRAM) or static memory (SRAM). In addition, the memory 712 may include any device for storing data, such as a disk drive or other non-volatile storage device, such as flash memory, solid state, or phase-change memory (PCM). In further embodiments, the functions and operations discussed with respect to processing an image to determine the moisture content of corn can be embodied in an application that is executed on the computer system 702 from the memory 712 and/or the storage 718. For example, the application can be made available through an "app store" for download and/or purchase. Once installed or made available for execution, computer system 702 can be specially configured to execute the processing an image to determine the moisture content of corn.

Computer system 702 also includes one or more interfaces 716 such as input devices (e.g., camera for capturing images), output devices and combination input/output devices. The interfaces 716 may receive input, provide output, or both. The storage 718 may include a computer-readable and computer-writeable nonvolatile storage medium in which instructions are stored that define a program to be executed by the processor. The storage system 718 also may include information that is recorded, on or in, the medium, and this information may be processed by the application. A medium that can be used with various embodiments may include, for example, optical disk, magnetic disk or flash memory, SSD, among others. Further, aspects and embodiments are not to a particular memory system or storage system.

In some embodiments, the computer system 702 may include an operating system that manages at least a portion of the hardware components (e.g., input/output devices, touch screens, cameras, etc.) included in computer system 702. One or more processors or controllers, such as processor 710, may execute an operating system which may be, among others, a Windows-based operating system (e.g., Windows NT, ME, XP, Vista, 7, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Sun Microsystems, or a UNIX operating systems available from various sources. Many other operating systems may be used, including operating systems designed for personal computing devices (e.g., iOS, Android, etc.) and embodiments are not limited to any particular operating system.

The processor and operating system together define a computing platform on which applications (e.g., "apps" available from an "app store") may be executed. Additionally, various functions for generating and manipulating images may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed components, or any combination thereof. Various embodiments may be implemented in part as MATLAB functions, scripts, and/or batch jobs. Thus, the invention is not limited to a specific programming language and any suitable programming language could also be used.

Although the computer system 702 is shown by way of example as one type of computer system upon which various functions for processing an image to determine the moisture content of corn may be practiced, aspects and embodiments are not limited to being implemented on the computer system, shown in FIG. 7. Various aspects and functions may be practiced on one or more computers or similar devices having different architectures or components than that shown in FIG. 7.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A method for determining moisture content of corn, the method comprising:
   processing a captured image of an ear of corn using a threshold value to create a segmented binary image comprising a first plurality of blobs;
   generating a luminance intensity profile across a region of the captured image containing at least one blob in the first plurality of blobs;
   determining, with reference to the luminance intensity profile, at least one characteristic of a plurality of corn kernels represented by the first plurality of blobs, the at least one characteristic including the location of the boundary of the at least one corn kernel; and
   estimating a moisture value for the ear of corn based on the at least one characteristic of the plurality of corn kernels.

2. The method of claim 1, wherein determining the location of the boundary of the at least one corn kernel includes:
   computing a derivative of the luminance intensity profile; and
   determining, with reference to the derivative of the luminance intensity profile, the location of the boundary of the at least one corn kernel.

3. The method of claim 1, wherein determining the at least one characteristic of the plurality of corn kernels represented by the first plurality of blobs further comprises:
   determining an average kernel width of a plurality of horizontally adjacent corn kernels in the plurality of corn kernels in the captured image;
   determining an average horizontal gap between a plurality of horizontally adjacent corn kernels in the plurality of corn kernels in the captured image; and
   determining a relationship of the average width to the average horizontal gap.

4. The method of claim 1, further comprising:
   processing a second captured image of a second ear of corn using a threshold value to create a second segmented binary image comprising a second plurality of blobs;
   determining a second at least one characteristic of a second plurality of corn kernels represented by the second plurality of blobs; and
   estimating a second moisture value for the second ear of corn based at least in part on the at least one characteristic of the second plurality of corn kernels; and
   determining an exponential decay curve that fits the first moisture value and the second moisture value using a least squares fitting technique.

5. The method of claim 4, further comprising:
   determining, for each of a plurality of candidate target moisture values, an estimated number of days by which a moisture value of corn will equal the candidate target moisture value;
   determining, for each of the plurality of candidate target moisture values, an estimated cost to harvest the corn on the estimated target date; and
   identifying an optimal target moisture value among the plurality of candidate target moisture values for which the cost to harvest the corn on the estimated target date for the candidate target moisture value is minimized.

6. The method of claim 5, wherein determining, for each of the plurality of candidate target moisture values, the estimated number of days by which the moisture value of corn will equal the candidate target moisture value further comprises:
   estimating an estimated number of growing degree units (GDUs) that must be accumulated to cause the corn to have the optimal target moisture value; and
   estimating the estimated number of days over which the number of GDUs will be accumulated.

7. The method of claim 6, wherein estimating the number of days over which the number of GDUs will be accumulated comprises accessing historical meteorological information relating to a geography in which the ear of corn is located.

8. The method of claim 6, further comprising:
   determining an actual number of GDUs accumulated during a day; and
   revising the estimated number of days over which the number of GDUs will be accumulated.

9. The method of claim 1, wherein estimating the moisture value for the ear of corn based on the at least one characteristic of the plurality of corn kernels comprises estimating an average depth of a plurality of indentations on the plurality of corn kernels in the captured image.

10. The method of claim 1, wherein estimating the moisture value for the ear of corn based on the at least one characteristic of the plurality of corn kernels comprises:
    determining a first reflectance value of light having a first wavelength from a stalk of the ear of corn, the first wavelength being sensitive to moisture;
    determining a second reflectance value of light having a second wavelength from the stalk of the ear of corn, the second wavelength being non-sensitive to moisture; and
    comparing the first reflectance value and the second reflectance value.

11. The method of claim 10, wherein determining the first reflectance value of light and the second reflectance value of light each comprises directing a laser beam at the stalk of the ear of corn.

12. An image processing system comprising:
    a memory;
    an image receiving component; and a processor configured to:
  process a captured image of an ear of corn using a threshold value to create a segmented binary image comprising a first plurality of blobs;
  generate a luminance intensity profile across a region of the captured image containing at least one blob of the first plurality of blobs;
  determine, with reference to the luminance intensity profile, at least one characteristic of a plurality of corn kernels represented by the first plurality of blobs, the at least one characteristic including the location of the boundary of the at least one corn kernel; and
  estimate a moisture value for the ear of corn based on the at least one characteristic of the plurality of corn kernels.

13. The image processing system of claim 12, wherein the processor being configured to determine the location of the boundary of the at least one corn kernel includes:
  computing a derivative of the luminance intensity profile; and
  determining, with reference to the derivative of the luminance intensity profile, the location of the boundary of the at least one corn kernel.

14. The image processing system of claim 12, wherein the processor is further configured to determine at least one characteristic of the plurality of corn kernels represented by the first plurality of blobs by acts further comprising:
  determining an average kernel width of a plurality of horizontally adjacent corn kernels in the plurality of corn kernels in the captured image;
  determining an average horizontal gap between a plurality of horizontally adjacent corn kernels in the plurality of corn kernels in the captured image; and
  determining a relationship of the average width to the average horizontal gap.

15. The image processing system of claim 12, wherein the image receiving component is a camera of a mobile device, wherein the processor is further configured to:
  determining a first reflectance value of light having a first wavelength from a stalk of the ear of corn, the first wavelength being sensitive to moisture;
  determining a second reflectance value of light having a second wavelength from the stalk of the ear of corn, the second wavelength being non-sensitive to moisture; and
  comparing the first reflectance value and the second reflectance value.

16. The image processing system of claim 15, further comprising a laser directing device, wherein determining the first reflectance value of light and the second reflectance value of light each comprises directing a laser beam at the stalk of the ear of corn.

17. The image processing system of claim 12, wherein the processor is further configured to:
  process a second captured image of a second ear of corn using a threshold value to create a second segmented binary image comprising a second plurality of blobs;
  determine at a second least one characteristic of a second plurality of corn kernels represented by the second plurality of blobs; and
  estimate a second moisture value for the second ear of corn based at least in part on the at least one characteristic of the second plurality of corn kernels.

18. The image processing system of claim 17, the processor further configured to:
  determine, for each of a plurality of candidate target moisture values, an estimated number of days by which a moisture value of corn will equal the candidate target moisture value;
  determine, for each of the plurality of candidate target moisture values, an estimated cost to harvest the corn on the estimated target date; and
  identify an optimal target moisture value among the plurality of candidate target moisture values for which the cost to harvest the corn on the estimated target date for the candidate target moisture value is minimized.

19. The image processing system of claim 18, the processor further configured to:
  estimate an estimated number of growing degree units (GDUs) that must be accumulated to cause the corn to have the optimal target moisture value; and
  estimate the estimated number of days over which the number of GDUs will be accumulated.

20. The image processing system of claim 19, the processor further configured to:
  determine an actual number of GDUs accumulated during a day; and
  revise the estimated number of days over which the number of GDUs will be accumulated.

* * * * *

UNITED STATES PATENT AND TRADEMARK OFFICE
CERTIFICATE OF CORRECTION

PATENT NO. : 10,157,472 B2  
APPLICATION NO. : 15/067750  
DATED : December 18, 2018  
INVENTOR(S) : Darrell L. Young et al.

Page 1 of 1

It is certified that error appears in the above-identified patent and that said Letters Patent is hereby corrected as shown below:

In the Specification

Column 15, Lines 41-42 should be corrected to read:
XML, REST, SOAP, CORBA IIOP, RMI, DCOM and Web Services.

Signed and Sealed this
Twenty-ninth Day of January, 2019

Andrei Iancu
*Director of the United States Patent and Trademark Office*